United States Patent [19]

Smits

[11] Patent Number: 4,479,500

[45] Date of Patent: Oct. 30, 1984

[54] PACING LEAD WITH A-V DISTANCE ADAPTER

[75] Inventor: Karel F. A. A. Smits, Oirsbeek, Netherlands

[73] Assignee: Medtronic, Inc., Minneapolis, Minn.

[21] Appl. No.: 418,926

[22] Filed: Sep. 16, 1982

[51] Int. Cl.³ ............................................. A61N 1/04
[52] U.S. Cl. ..................................... 128/786; 128/785
[58] Field of Search ............................... 128/784–786, 128/419 P

[56] References Cited

U.S. PATENT DOCUMENTS 3,865,118  2/1975  Bures ........................... 128/419 P X
4,289,144  9/1981  Gilmen .................................. 128/785
4,393,883  7/1983  Smyth et al. ......................... 128/785

FOREIGN PATENT DOCUMENTS 0004667  10/1979  European Pat. Off. ............ 128/786

Primary Examiner—Lee S. Cohen
Attorney, Agent, or Firm—Reed A. Duthler; Joseph F. Breimayer; John L. Rooney

[57] ABSTRACT

A single pass atrial-ventricular endocardial lead for transvenous insertion. A ventricular electrode is mounted at the distal end of a ventricular lead sheath and an atrial electrode is mounted at the distal end of an atrial lead sheath which is slideably mounted around the ventricular lead sheath. A connector assembly is mounted at the proximal end of the atrial lead sheath. An adjustment device is provided to allow axial adjustment of the ventricular lead sheath relative to the atrial lead sheath without modification to or adjustment of the connector assembly prior to attachment to an implantable pulse generator.

13 Claims, 11 Drawing Figures

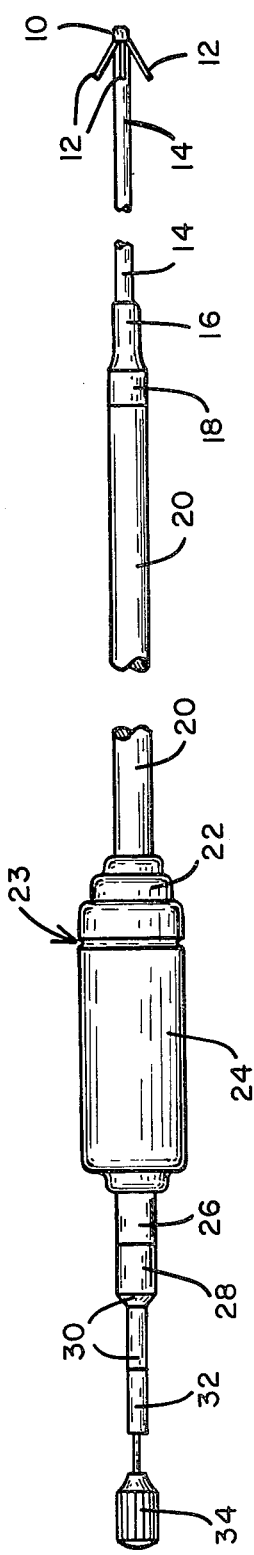
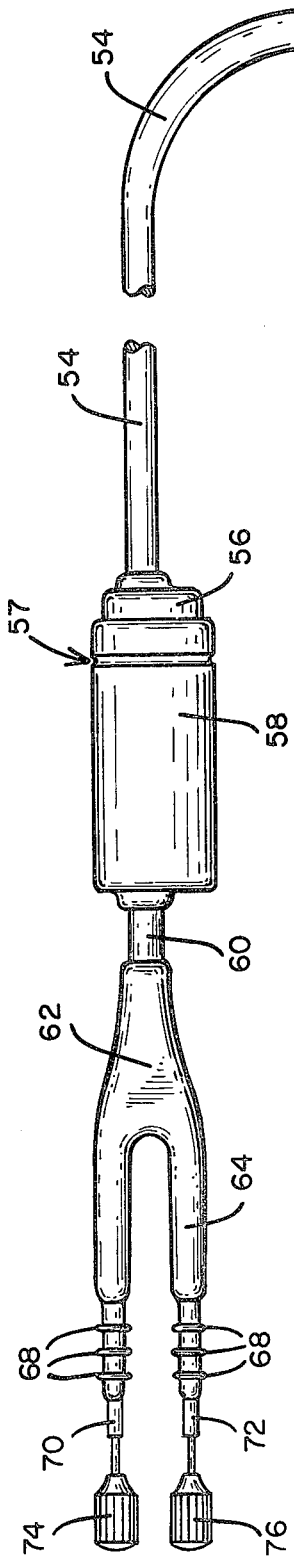
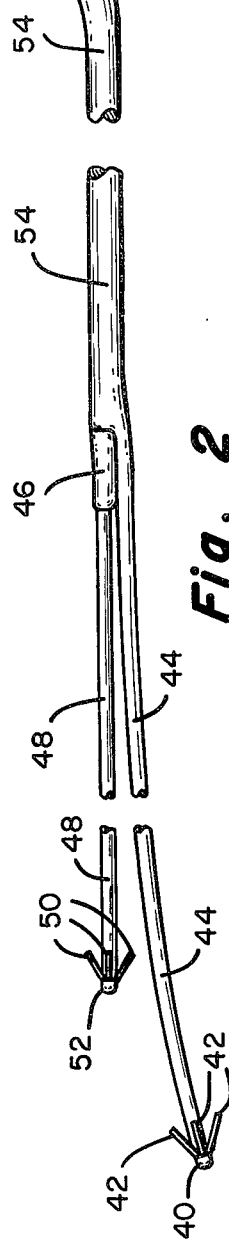

4,479,500

PACING LEAD WITH A-V DISTANCE ADAPTER

BACKGROUND OF THE INVENTION

1. Field of the Invention

The present invention pertains to a surgical applicator, and more particularly to an atrial-ventricular endocardial lead.

2. Description of the Prior Art

Early cardiac pacemakers utilized electrical stimulation of a single chamber of the heart, typically the right ventricle. Single chamber stimulation is still the most prevalent pacing technique. However, a number of medical conditions are more effectively treated using stimulation of two chambers of the heart or by sensing in one chamber and stimulating another. These techniques typically utilize the right ventricle and the right atrium, and generally use a separate pacing lead for each chamber. This approach is relatively convenient in epicardial applications, but is often problematical in endocardial applications in which the leads are inserted transvenously. Single pass atrial-ventricular pacing leads have been designed to avoid these problems.

Because internal heart anatomy varies among individuals, a number of atrial-ventricular leads utilize atrial and ventricular electrodes which are adjustable relative to one another. Several current designs encase both atrial and ventricular conductors in a commmon outer sheath with either the atrial or the ventricular conductor slideably mounted within the outer sheath, allowing axial adjustment of the relative positions of the electrodes. In present designs, this adjustment method often results in difficulties or complexities in attaching the lead to implantable pulse generators.

An early single pass atrial ventricular lead is taught by Bures in U.S. Pat. No. 3,865,118. In this lead, the ventricular lead sheath is slideably mounted within the atrial lead sheath. Electrodes are attached to the distal portions of the atrial and ventricular sheaths and electrical connectors are attached to the proximal ends of these sheaths. Movement of the ventricular electrode relative to the atrial electrode therefore results in movement of the ventricular connectors relative to the atrial connectors. Present implantable pulse generators, however, employ connector assemblies with electrical connectors in fixed relation to one another. If the arrangement of electrical connectors on the lead does not correspond to the arrangement of electrical connectors on the pulse generator, attachment to the pulse generator may be precluded. If attachment is possible, it generally requires deformation of the lead to mate the connectors, which stresses the lead and may lead to fracture of the lead conductor. Because the arrangement of connectors is variable on the Bures lead, the probability of such difficulties is increased.

Another early single pass atrial ventricular lead is taught by Sabel in U.S. Pat. No. 3,949,757. In this lead, the atrial sheath is slideably mounted within the ventricular sheath. As with the Bures lead, adjustment of the relative positions of the electrodes changes the relative positions of the electrical connectors, with the disadvantages discussed above.

A more recent single pass atrial ventricular lead that overcomes some of the problems of the Bures and Sabel leads is taught by Gilman in U.S. Pat. No. 4,289,144. In this lead, the ventricular sheath is slideably mounted within the atrial sheath. Mounted at the proximal end of the lead is a bifurcated connector assembly with two connector sleeves. One connector sleeve carries a connector pin coupled to the atrial electrode by means of a conductor. The proximal end of the ventricular sheath slideably protrudes from the other connector sleeve. After the lead is adjusted, the protruding ventricular sheath and the conductor within it are trimmed and an electrical connector pin is attached to the proximal end of the conductor, a time consuming procedure. Because the arrangement of the two connector pins then corresponds to the arrangement of the electrical connectors on typical pulse generators, attachment is easily accomplished without stress to the lead. After attachment, further adjustment of the lead is precluded, as the ventricular sheath and conductor are then fixed.

A further problem common to several single pass A-V leads is that of sealing the lead at the exit point of the inner sheath. In leads such as the Gilman lead, where a conductor is exposed to the lumen of the outer sheath, a fluid path from that lumen to the exterior of the lead raises the risk of current leakage.

SUMMARY OF THE INVENTION

The present invention provides a single pass atrial-ventricular lead that overcome the problems identified in the prior art structures. The outer lead sheath has an adjustment means for altering the length of the sheath, such as a circumferentially pleated sheath segment or slideably overlapping sheath segments. A first conductor mounted within the outer lead sheath has means for allowing variation of its length, such as a large diameter coiled segment having increased axial flexibility. The outer sheath is slideably mounted around the inner sheath with the inner sheath protruding therefrom. The inner sheath is fixed relative to the proximal end of the outer sheath so that variation in the length of the outer sheath alters the relationship of electrodes attached to the distal ends of the inner and outer sheaths. A connector assembly is attached to the proximal end of the outer sheath. The outer sheath may be fixed relative to the inner sheath by engagable projections and indentations on the inner and outer sheaths or by a suture.

By incorporating such adjustment means, the relative positions of the outer and inner sheaths may be adjusted without corresponding movement of the electrical connectors. This allows use of a connector assembly with electrical connectors in fixed relationship to one another which simplifies attachment to current pulse generators and eliminates the need for cutting or other modifications to the connector assembly before attachment. Because the adjustment means is independent of the connector assembly, further adjustment of the lead can be accomplished after attachment to a pulse generator.

The outer sheath is sealed against ingress of fluids at the exit point of the inner sheath by means of a roller collar which is attached to both sheaths. The provision of a roller collar prevents electrical leakage due to fluid ingress.

These and other features of the present invention are depicted in the several embodiments of the invention illustrated in the drawings.

BRIEF DESCRIPTION OF THE DRAWINGS

FIG. 1 is a plan view of a single pass lead incorporating the present invention in which the ventricular sheath is mounted coaxially within the atrial conductor and in which the means for adjusting the length of the atrial sheath is a slideable adjuster assembly.

FIG. 2 is a plan view of single pass lead incorporating the present invention in which the atrial and ventricular conductors lie parallel to one another within the atrial sheath and in which the means for adjusting the length of the atrial sheath is a slideable adjuster assembly.

DETAILED DESCRIPTION OF THE PREFERRED EMBODIMENTS

Figure 3:
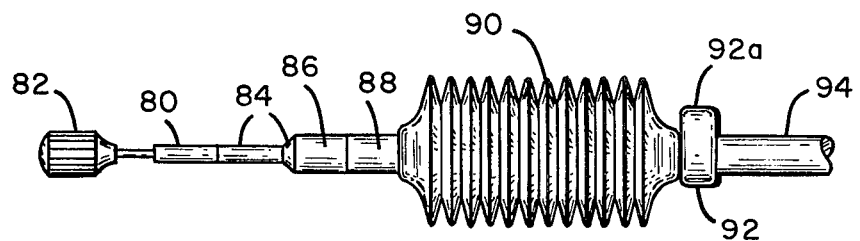
FIG. 3 is a plan view of the proximal end of a single pass lead incorporating the present invention in which the ventricular sheath is mounted coaxially within the atrial conductor, and in which the means for adjusting the length of the atrial sheath is a plurality of circumferential pleats in the atrial sheath.

The present invention is described in preferred embodiments having the ventricular sheath within the atrial sheath. However, configurations having the atrial sheath within the ventricular sheath are within the intended scope of the invention. The present invention is further described in coaxial embodiments employing atrial ring electrodes and in-line connector assemblies and in parallel embodiments employing atrial tip electrodes and bifurcated connector assemblies. However, configurations employing different combinations of these elements are within the intended scope of the invention. Finally, the present invention is described in its preferred embodiments as having unipolar atrial and ventricular electrodes. However, configurations employing bipolar electrodes are within the intended scope of the invention.

CONSTRUCTION

FIG. 1 is a plan view of a first embodiment of a lead incorporating the present invention. In this embodiment, an in-line connector assembly and coaxial atrial and ventricular conductors are illustrated in cooperation with a slideable adjuster assembly for adjusting the relative positions of the atrial and ventricular electrodes.

Ventricular electrode 10 is mounted at the distal end of ventricular sheath 14 which is further comprised of tines 12 and which protrudes from first atrial sheath segment 20. Atrial electrode 18 is a ring electrode encircling the distal end of first atrial sheath segment 20 which is slideably mounted around ventricular sheath 14. Fixedly attached to both first atrial sheath segment 20 and ventricular sheath 14 is roller collar 16 which seals the exit point of ventricular sheath 14 against ingress of fluids. Fixedly attached to the proximal end of first atrial sheath segment 20 is first atrial sheath end 22, which is slideably overlapped by second atrial sheath end 24, which is fixedly attached to the distal end of second atrial sheath segment 26 and is further comprised of suture groove 23. The proximal end of second atrial sheath segment 26 is fixedly attached to an in-line connector assembly. The in-line connector assembly is comprised of first electrical connector 28, insulation 30, and second electrical connector 32. First electrical connector 28 is coupled to atrial electrode 18 by means of a first space-wound coil (not visible). Second electrical connector 32 is coupled to ventricular electrode 10 by means of a second space-wound coil (not visible). Stylet 34 is inserted through an aperture in second electrical connector 32 and proceeds through the second space-wound coil to the distal end of ventricular sheath 14.

Atrial and ventricular sheath elements 14, 16, 20, 22, and 24, along with insulation 30 and tines 12 are preferably made of a flexible biocompatible plastic such as polyurethane or silicone rubber. Electrodes 10 and 20 are preferably made of an inert conductive metal such as platinum or an alloy thereof.

FIG. 2 is a plan view of a further embodiment of a lead incorporating the present invention. In this embodiment a bifurcated connector assembly and parallel atrial and ventricular conductors are illustrated in cooperation with slideable adjuster assembly for adjusting the relative positions of the atrial and ventricular electrodes.

Ventricular electrode 52 is mounted at the distal end of ventricular sheath 48 which is provided with tines 50 and which protrudes from first atrial sheath segment 54. Atrial electrode 40 is mounted at the distal end of first atrial sheath segment 54 which has a "J" shaped bend 44 in its distal portion and which is provided with tines 42. Fixedly attached to both first atrial sheath segment 54 and ventricular sheath 48 is roller collar 46 which seals the exit point of ventricular sheath 48 against ingress of fluids. Fixedly attached to the proximal end of first atrial sheath segment 54 is first atrial sheath end 56 which is slideably overlapped by second atrial sheath end 58 which is fixedly attached to the distal end of second atrial sheath segment 60 and is further comprised of suture groove 57. The proximal end of second atrial sheath segment 60 is fixedly attached to a bifurcated connector assembly. The bifurcated connector assembly is comprised of connector pins 70 and 72, sealing rings 68, and insulation 62. Connector pin 72 is coupled to atrial electrode 40 by means for a first space-wound coil (not visible). Connector pin 70 is coupled to ventricular electrode 52 by means of a second space-wound coil (not visible). Stylets 76 and 74 are inserted through apertures in connector pins 72 and 70 and proceed through the first and second space-wound coils respectively to the distal ends of first atrial sheath segment 54 and ventricular sheath 48 respectively.

Atrial and ventricular sheath elements 46, 48, 54, 56, 58, and 60, along with insulation 62, and tines 42 and 50, are preferably made of a biocompatible flexible plastic such as silicone rubber or polyurethane. Electrodes 40 and 52 may be made of an inert conductive metal such as platinum or an alloy thereof.

FIG. 3 is a plan view of the proximal portion of a lead illustrating a further embodiment of the present invention. In this embodiment an in-line connector assembly and coaxial atrial and ventricular conductors are illustrated in cooperation with a pleated adjuster assembly for adjusting the relative positions of the atrial and ventricular electrodes. The distal portion of this lead is identical to that of the lead shown in FIG. 1.

Atrial sheath fixation mechanism 92 encircles first atrial sheath segment 94 and is further comprised of protrusion 92a. Fixedly attached to the proximal end of first atrial sheath segment 94 is pleated atrial sheath segment 90 which is fixedly attached to the distal end of second atrial sheath segment 88. The proximal end of second atrial sheath segment 88 is fixedly attached to an in-line connector assembly. The in-line connector assembly is comprised of first electrical connector 86, insulation 84, and second electrical connector 80. First electrical connector 86 is coupled to first space-wound coil (not visible). Stylet 82 is inserted through an aperture in second electrical connector 80 and proceeds through a second space-wound coil (not visible) to the distal end of the ventricular sheath.

Expandable segment 90 and fixation mechanism 92 are preferably made of polyurethane or silicone rubber. Other lead components are of materials identical to those of the lead of FIG. 1.

Figure 4:
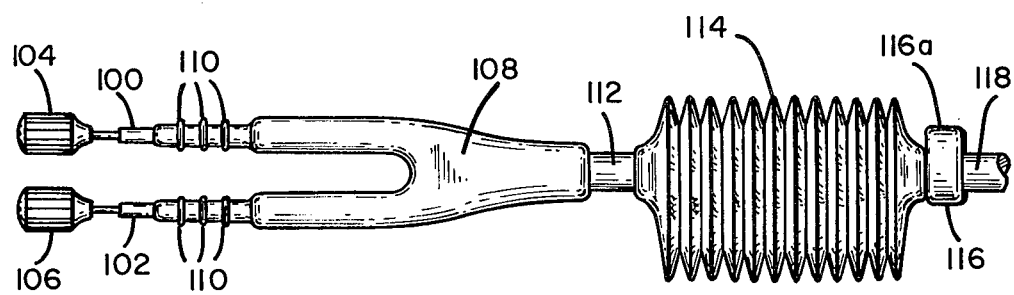
FIG. 4 is a plan view of the proximal end of a single pass lead incorporating the present invention in which the atrial and ventricular conductors lie parallel to one another within the atrial sheath and in which means for adjusting the length of the atrial sheath is a plurality of circumferential pleats in the atrial sheath.

FIG. 4 is a plan view of the proximal portion of a lead illustrating a further embodiment of the present invention. In this embodiment, a bifurcated connector assembly and parallel atrial and ventricular conductors are illustrated in combination with a pleated adjuster assembly for adjusting the relative positions of the atrial and ventricular electrodes. The distal portion of this lead is identical to that of the lead shown in FIG. 2.

Atrial sheath fixation mechanism 116 encircles first atrial sheath segment 118 and is further comprised of protrusion 116a. Fixedly attached to the proximal end of first atrial sheath segment 118 is pleated atrial sheath segment 114 which is fixedly attached to the distal end of second atrial sheath segment 112. The proximal end of second atrial sheath segment 112 is fixedly attached to a bifurcated connector assembly. The bifurcated connector assembly is comprised of connector pins 100 and 102, sealing rings 110 and insulation 108. Connector pin 102 is coupled to a first space-wound coil (not visible). Connector pin 100 is coupled to a second space-wound coil (not visible). Stylets 106 and 104 are inserted through apertures in connector pins 102 and 100 and proceed through first and second space-wound coils respectively to the distal ends of first atrial sheath segment 118 of the ventricular sheath.

Expandable segment 114 and fixation mechanism 116 are preferably made of polyurethane or silicone rubber. Other lead components are of materials identical to those of the lead of FIG. 2.

Figure 5:
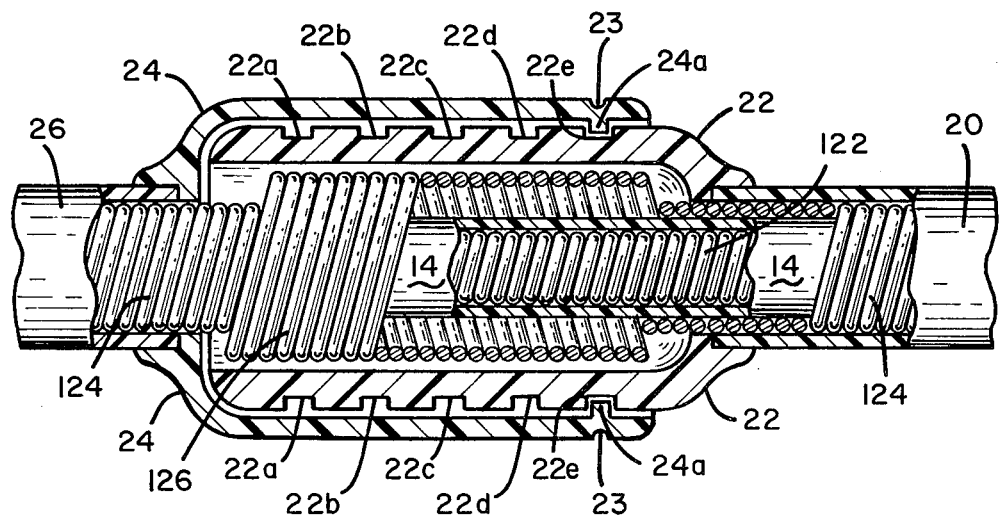
FIG. 5 is a cutaway view of the adjustment means of the lead shown in FIG. 1.

FIG. 5 is a cutaway view of the adjustment means of the lead pictured in FIG. 1. First atrial sheath segment 20, second atrial sheath segment 26 and ventricular sheath 14 are cylindrical members, each having a lumen. First atrial sheath segment 20 is mounted slideably with respect to ventricular sheath 14. Second atrial sheath segment 26 is mounted fixedly with respect to ventricular sheath 14. First atrial sheath end 22 is further comprised of a series of O-ring grooves 22a, b, c, d, and e. Second atrial sheath end 24 is further comprised of an O-ring 24a engagable with O-ring grooves 22a, b, c, d, and e and of a suture groove 23. First space-wound coil 124 is fixedly mounted within first atrial sheath segment 20 and second atrial sheath segment 26 and extends between electrical connector 28 and electrode 18 (FIG. 1). First space-wound coil 124 is further comprised of a large diameter segment 126 having increased axial flexibility over the rest of first space-wound coil 124. Second space-wound coil 122 is mounted within ventricular sheath 14 and extends between electrical connector 32 and electrode 10 (FIG. 1). O-ring grooves 22a, b, c, d, and e and O-ring 24a provide means for stabilizing and sealing the lead at various adjustment points.

Figure 6:
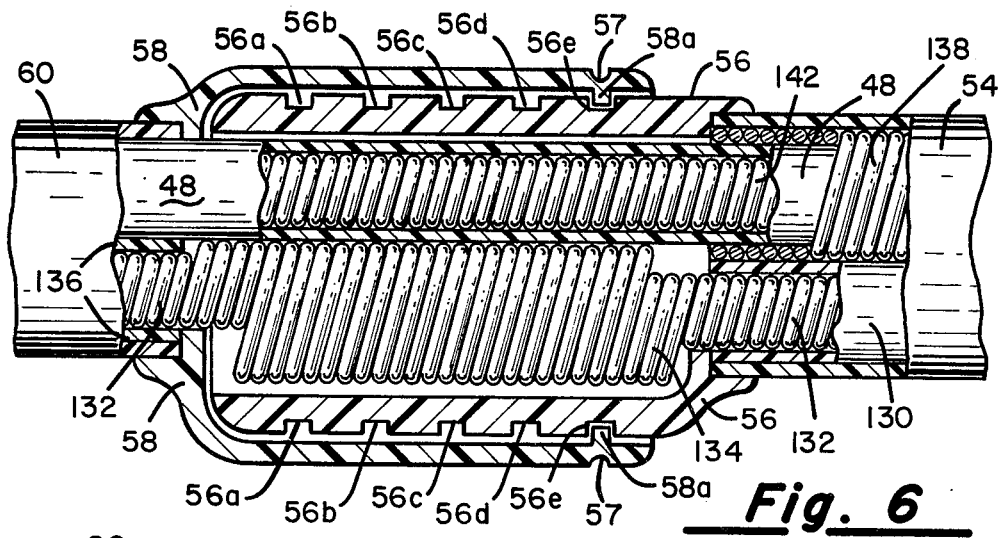
FIG. 6 is a cutaway view of the adjustment means of the lead shown in FIG. 2.

FIG. 6 is a cutaway view of the adjustment means of the lead pictured in FIG. 2. First atrial sheath segment 54 and second atrial sheath segment 60 are flattened cylindrical members each having a lumen. Ventricular sheath 48 and atrial insulators 130 and 136 are cylindrical members each having a lumen. First atrial sheath segment 54 is mounted slideably with respect to ventricular sheath 48. Second atrial sheath segment 60 is mounted fixedly with respect to ventricular sheath 48. First atrial sheath end 56 is further comprised of a series of O-ring grooves 56a, b, c, d, and e. Second atrial sheath end 58 is further comprised of an O-ring 58a engageable with O-ring grooves 56a, b, c and d of a suture groove 57. First space-wound coil 132 extends between connector pin 72 and electrode 40 (FIG. 2) and is mounted within first atrial sheath segment 54 and second atrial sheath segment 60. First space-wound coil 132 is further comprised of a large diameter segment 134 having increased axial flexibility over the rest of first space-wound coil 132. Second space-wound coil 142 is mounted within ventricular sheath 36 and extends between connector pin connector pin 70 and electrode 52. Third space-wound coil 138 is fixedly mounted within first atrial sheath segment 30 encircling ventricular sheath 48, allowing first atrial sheath segment 54 to slide freely. O-ring grooves 56a, b, c, d and e, and O-ring 58a provide means for stabilizing and sealing the lead at various adjustment points.

Figure 7:
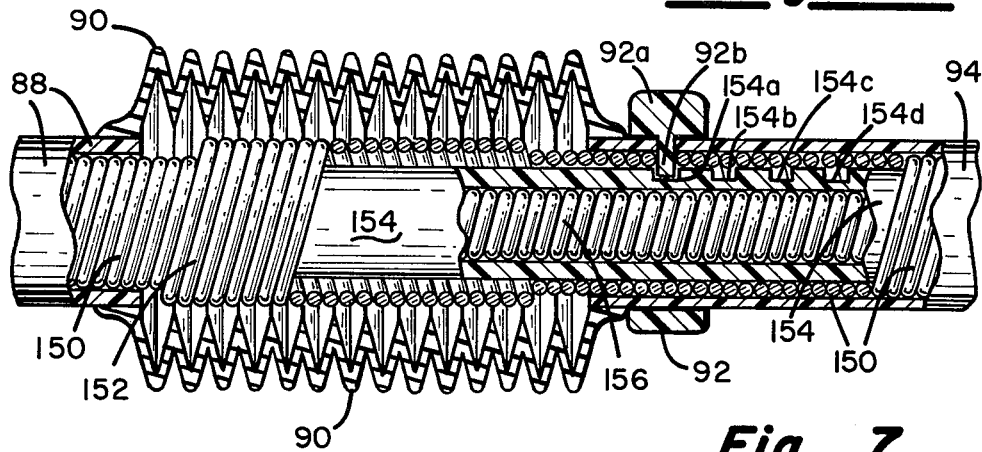
FIG. 7 is a cutaway view of the adjustment means of the lead in FIG. 3.

FIG. 7 is a cutaway view of the adjustment means of the lead pictured in FIG. 3. First atrial sheath segment 94, second atrial sheath segment 88 and ventricular sheath 154 are tubular members. First atrial sheath segment 94 is mounted slideably relative to ventricular sheath 154. Second atrial sheath segment 88 is mounted fixedly relative to ventricular sheath 154. Pleated atrial sheath segment 90 is fixedly attached to first atrial sheath segment 94 and second atrial sheath segment 88. Atrial sheath fixation mechanism 92 encircles first atrial sheath segment 94 and is further comprised of a projection 92b. Ventricular sheath 154 is further comprised of indentations 154a, b, c and d engagable with projection 92b. First space-wound coil 150 is mounted within first atrial sheath segment 94 and second atrial sheath segment 88 and extends between electrical connector 102 (FIG. 3) and the atrial electrode. First space-wound coil 150 is further comprised of a large diameter segment 152, having increased axial flexibility over the rest of space-wound coil 150. Second space-wound coil 156 is mounted within ventricular sheath 154 and extends between electrical connector 100 (FIG. 3) and the ventricular electrode. Indentations 154a, b, c, and d and projection 92b provide means for sealing and stabilizing the lead at various adjustment points.

Figure 8:
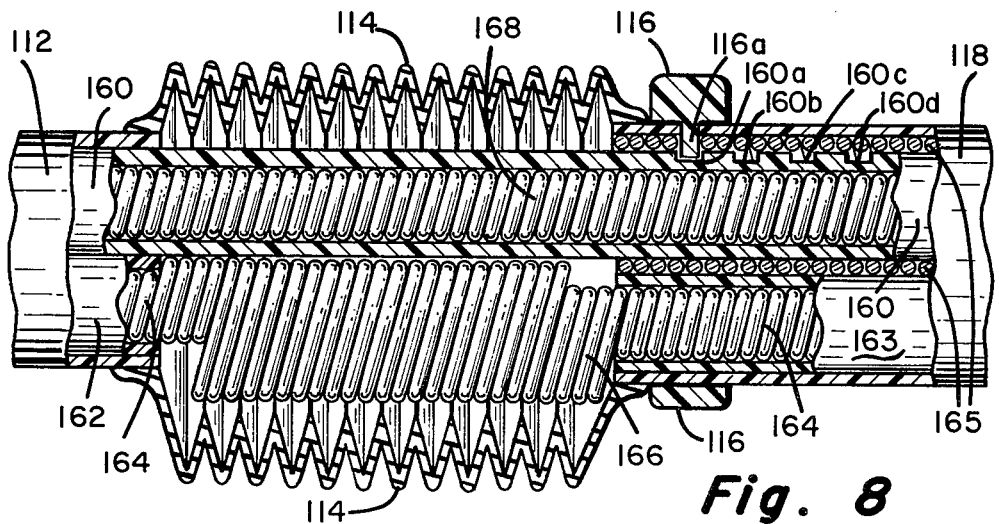
FIG. 8 is a cutaway view of the adjustment means of the lead shown in FIG. 4.

FIG. 8 is a cutaway view of the adjustment means of the lead pictured in FIG. 4. First atrial sheath segment 118 and second atrial sheath segment 112 are flattened tubular members. Ventricular sheath 160 and atrial insulators 162 and 163 are tubular members. First atrial sheath segment 118 is mounted slideably relative to ventricular sheath 160. Second atrial sheath segment 112 is mounted fixedly relative to ventricular sheath 160. Pleated atrial sheath segment 114 is fixedly attached to first atrial sheath segment 118 and second atrial sheath segment 112. Atrial sheath fixation mechanism 116 encircles first atrial sheath segment 118 and is further comprised of a projection 116. Ventricular sheath 160 is further comprised of indentations 160a, b, c, and d engagable with projection 116. First space-wound coil 164 is fixedly mounted within first atrial sheath segment 118 and second atrial sheath segment 112 and extends between connector pin 102 (FIG. 4) and the atrial electrode. First space-wound coil 164 is further comprised of a large diameter segment 166 having increased axial flexibility over the remainder of first space-wound coil 164. Second space-wound coil 168 is mounted within ventricular sheath 160 and extends between connector pin 100 (FIG. 4) and the ventricular electrode. Third space-wound coil 165 is mounted fixedly within first atrial sheath segment 118 encircling ventricular sheath 160 allowing first atrial sheath segment 118 to slide freely. Indentations 160a, b, c, and d and projection 116a provide means for stabilizing the lead at those various adjustment points.

Figure 9:
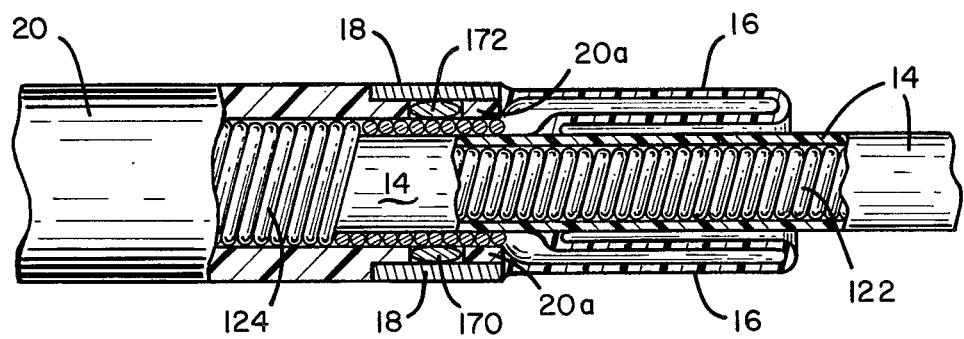
FIG. 9 shows the exit point of the ventricular sheath in the lead shown in FIG. 1.

FIG. 9 is a cutaway view of the region in which ventricular sheath 14 exits first atrial sheath segment 20 through aperture 20a in the lead pictured in FIG. 1. Atrial electrode 18 encircles the distal end of first atrial sheath 20 and is coupled to first space-wound coil 124 by means of wires 170 and 172. First atrial sheath segment 20 ends in aperture 20a. Attached to first atrial sheath segment 20 and ventricular sheath 14 is roller collar 16 which seals aperture 20a against ingress of fluids. Second space-wound coil 122 is mounted within ventricular sheath 14.

Figure 10:
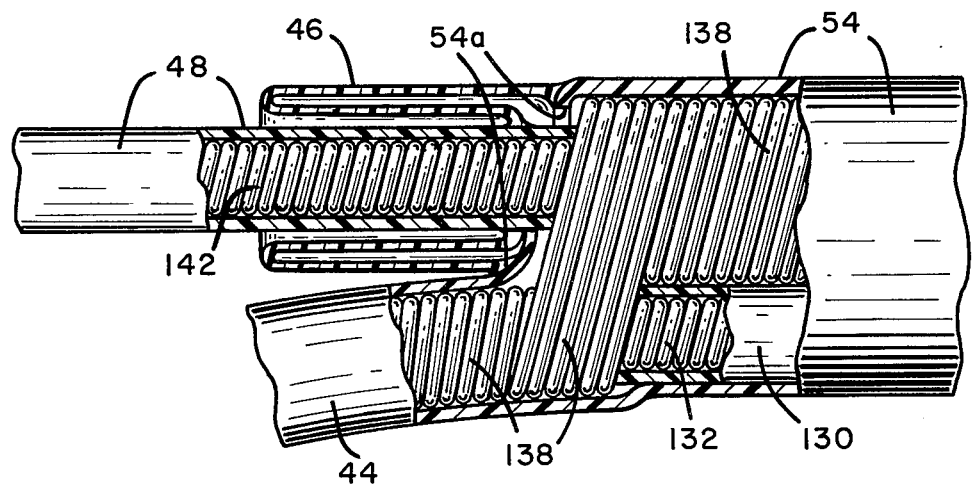
FIG. 10 shows the exit point of the ventricular sheath in the lead shown in FIG. 2.

FIG. 10 is a cutaway view of the region in which ventricular sheath 48 exits first atrial sheath segment 54 through aperture 54a in the lead pictured in FIG. 2. First space-wound coil 132 is mounted within first atrial sheath segment 54 and second space-wound coil 142 is mounted within ventricular sheath 48. Distal to aperture 54a, third space-wound coil 138 is a memory coil having a "J" shape which imparts "J" shaped bend 44 (FIG. 2) to first atrial sheath segment 54. Roller collar 46 is fixedly attached to first atrial sheath segment 54 and to ventricular sheath 48, sealing aperture 54a against ingress of fluids.

Figure 11:
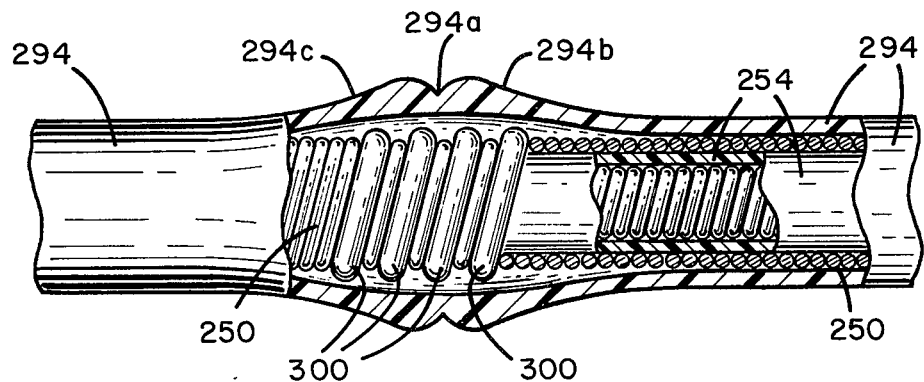
FIG. 11 shows an alternate fixation mechanism to be used with the adjustment means shown in FIGS. 3 and 4.

FIG. 11 is a cutaway view of an alternative fixation mechanism to that shown in FIGS. 3, 4, 7 and 8. Instead of matching protrusions from the atrial sheath and indentations on the ventricular sheath, a suture is used to stabilize the two sheaths. Because the conductor coils are radially stiff, a radially compressible member must span the distance between the inner and outer sheaths in the vicinity of the suture groove. In its preferred embodiment this compressible member is a short coil of soft polymer wire, such as polyurethane, of larger diameter than the lead coil. By keeping the polymer coil short, the added friction caused by the coil is minimized. Other compressible members such as protrusions from the atrial sheath are also believed to be within the scope of the invention.

Lead elements correspond to those of FIG. 7, however the fixation mechanism is clearly applicable to the lead of FIG. 8 as well.

First atrial sheath segment 294 is provided with a suture groove 294a. On either side of the groove are ramps 294b and 294c, which distribute the force of the suture. Polymer coil 300 is shown interwound with first conductor 250. Ventricular sheath 254 is surrounded by polymer coil 300.

The conductors shown in FIGS. 5 through 10 are illustrated as quadrifilar coils. For unipolar leads, the individual wires within a quadrifilar coil need not be insulated from one another. However, if a bipolar embodiment is required, mutual insulation of the individual wires within a coil will provide a method of accomplishing this end without adding to the cross section of the lead. The coils are may be made of MP35N alloy, or other conductors known to the art.

PREFERRED MODES OF OPERATION

For leads of the parallel conductor embodiment set forth in FIG. 2 the preferred mode of operation is as follows. Stylets 74 and 76 are inserted into the lead, stylet 76 straightening the J-shaped bend 44 in first atrial sheath segment 54. Under flouroscopy, the lead is introduced into a vein leading to the right atrium, subsequently pushed through into the atrium by stylet 76. Removal of stylet 76 allows the distal portion of first atrial sheath segment 54 to resume its "J" shaped bend 44. Atrial electrode 40 is positioned and measurements are taken until it is securely positioned in a location having adequate electrical thresholds. After satifactorily securing atrial electrode 40, ventricular lead sheath 48 is advanced into the right ventricle care being taken to avoid dislodging atrial electrode 40. The slideable adjuster is adjusted so that ventricular electrode 52 may be securely lodged in the ventricle without disturbing atrial electrode 40 in the atrium. Thresholds are taken and ventricular electrode 52 is repositioned as required. After both electrodes are satisfactorily positioned, stylet 74 is removed. First atrial sheath segment 54 is anchored at the vein incision site and the venous incision is closed. The bifurcated connector assembly is coupled to a pulse generator in the normal fashion and the pulse generator is secured within the body. The procedure for operating the lead of FIG. 4 is identical with the exception that the pleated adjuster is used.

The preferred mode of operation of leads of the coaxial embodiment illustrated in FIG. 1 is as follows. The lead is introduced into a vein leading to the right atrium. Under flouroscopy, ventricular electrode 10 is advanced through the tricuspid valve and is positioned in the ventricular cavity of the heart. Thresholds are taken and the ventricular electrode 10 is repositioned as necessary. Following placement of ventricular electrode 10, atrial electrode 18 is positioned in the atrium by use of the slideable adjuster. Threshold readings are taken and atrial electrode 18 is repositioned as necessary. After both electrodes are satisfactorily positioned, stylet 34 is removed. First atrial sheath segment 20 is anchored at the venous incision site and the venous incision is closed. The in-line connector assembly is coupled to a pulse generator in the normal fashion, and the pulse generator is secured within the body. The operation of the lead pictured in FIG. 3 is identical with the exception that the pleated adjuster is used.

Adjustment of leads using the slideable adjuster assembly of FIGS. 1 and 2 is accomplished by sliding the first atrial sheath end relative to the second atrial sheath end until appropriately adjusted. Engagement of O-rings with O-ring grooves stabilizes and seals the lead. A suture may optionally be placed around the suture groove to provide additional security.

Adjustment of leads using the pleated adjuster assembly of FIGS. 3 and 4 is accomplished by sliding the first atrial sheath segment relative to the second atrial sheath segment. By pulling out on the external protrusion on the atrial sheath fixation mechanism, the internal protrusion is disengaged from the indentations on the ventricular sheath, easing the sliding process.

Having thus described the invention, there is claimed as new and desired to be secured by Letters Patent:

1. A lead for dual chamber pacing comprising:
   an insulated first sheath having a proximal end and a distal end;
   a first conductor, having a proximal end and a distal end, mounted within said first sheath;
   a first electrode electrically coupled to the distal end of said first conductor, exposed to the exterior of the distal end of said first sheath;
   a connector assembly mounted fixedly to the proximal end of said first sheath comprising:
      a first connector electrically coupled to the proximal end of said first conductor; and
      a second connector;
   an insulated second sheath having a proximal end, a distal end, a lumen, and an aperture connecting said lumen to the exterior of said second sheath, distal to the proximal end of said second sheath, said second sheath mounted slideably around said first sheath, the proximal end of said second sheath fixedly attached to said connector assembly, the distal end of said first sheath exiting through and protruding from the aperture of said second sheath;
   a first expandable means for variation of the length of the portion of said second sheath lying between the proximal end of said second sheath and the aperture of said second sheath whereby the distance said first sheath protrudes from the aperture of said second sheath may be varied;
   a second conductor, having a proximal end and a distal end, mounted within said second sheath exterior to said first sheath, electrically coupled to said second connector;
   a second expandable means for allowing variation of the length of said second conductor, said second expandable means comprising a segment of said second conductor having axial flexibility; and
   a second electrode coupled to the distal end of said second conductor, exposed to the exterior of said second sheath.

2. A lead according to claim 1 wherein said first conductor comprises a first space-wound coil and said second conductor comprises a second space-wound coil having a first diameter.

3. A lead according to claim 2 wherein said second expandable means comprises a segment of said second space-wound coil having a second diameter greater than the first diameter of said second space-wound coil whereby said segment has increased axial flexibility and is readily variable in length.

4. A lead according to claim 3 wherein said first expandable means comprises one or more circumferential pleats in said second sheath distal to the proximal end of said second sheath and proximal to the aperture of said second sheath, whereby said second sheath is variable in length.

5. A lead according to claim 4 wherein said second sheath further comprises a projection into the lumen of said second sheath distal to said circumferential pleats and wherein said first sheath further comprises one or more indentations engageable by said projection whereby said first sheath may be stabilized relative to said second sheath.

6. A lead according to claim 4 wherein said second sheath further comprises an exterior circumferential groove distal to said circumferential pleats, proximal to the aperture of said second sheath, and a compressible means spanning the distance between said second sheath and said first sheath, located concentric to said circumferential groove, whereby a suture may be used to stabilize said first sheath relative to said second sheath.

7. A lead according to claim 6 wherein said second compressible means is a coil of polymer wire, encircling said first sheath.

8. A lead according to claim 4 further comprising a roller collar sealably attached to said second sheath surrounding the aperture of said second sheath and sealably attached to and surrounding said first sheath, whereby the aperture of said second sheath is sealed against ingress of body fluids.

9. A lead according to claim 3 wherein said first expandable means comprises said second sheath further comprised of:
   a first segment having a proximal end and a distal end, the distal end of said first segment attached to said second electrode, the proximal end of said first segment extending proximal of the aperture of said second sheath; and
   a second segment having a proximal end and a distal end, the proximal end of said second segment attached to the said second connector and a distal end of said second segment slideably overlapping the proximal end of said first segment whereby said second sheath is variable in length.

10. A lead according to claim 9 wherein said second segment is further comprised of a projection located at the distal end of said second segment and wherein said first segment is further comprised of one or more indentations located at the proximal end of said first segment engagable with said projection whereby said first segment may be stabilized relative to said second segment.

11. A lead according to claim 10 wherein said projection comprises an O-ring and wherein said indentations comprise O-ring grooves whereby engagement of said O-ring and said O-ring grooves stabilizes said first segment with respect to said second segment and seals the junction of said first segment and said second segment from inflow of body fluids.

12. A lead according to claim 9 wherein said second segment is further comprised of an exterior circumferential groove located on that portion of said second segment which overlaps said first segment whereby said first segment may be stabilized relative to said second segment by use of a suture.

13. A lead according to claim 9 further comprising a roller collar sealably attached to said second sheath surrounding the aperture of said second sheath and sealably attached to and surrounding said first sheath whereby the aperture of said second sheath is sealed against ingress of body fluids.

* * * * *